United States Patent [19]
Siuciak et al.

[11] Patent Number: 5,827,823
[45] Date of Patent: Oct. 27, 1998

[54] METHOD OF PRODUCING ANALGESIA USING NEUROTROPHINS

[75] Inventors: Judith Siuciak, Tarrytown; Charles A. Altar, Katonah; Ronald M. Lindsay, Briarcliff Manor, all of N.Y.

[73] Assignee: Regeneron Pharmaceuticals, Inc., Tarrytown, N.Y.

[21] Appl. No.: 378,079

[22] Filed: Jan. 25, 1995

Related U.S. Application Data

[63] Continuation of Ser. No. 110,399, Aug. 23, 1993, abandoned, which is a continuation-in-part of Ser. No. 944,823, Sep. 14, 1992, abandoned.

[51] Int. Cl.$^6$ .......................... A61K 38/10; A61K 35/30
[52] U.S. Cl. ................... 514/12; 514/2; 514/21; 514/816; 514/817; 514/818; 424/570
[58] Field of Search ................... 514/2, 21, 12, 514/816, 817, 818; 424/570, 450

[56] References Cited

U.S. PATENT DOCUMENTS

| | | | |
|---|---|---|---|
| 4,753,635 | 6/1988 | Sagan et al. | 604/49 |
| 5,073,543 | 12/1991 | Marshall et al. | 514/21 |

OTHER PUBLICATIONS

Goldstein et al (1986) Scientific Amer. 255: 74–83.
Gregoriadis et al (1993) Tieudsin Biotech. 11: 440–442.
Working, P.K. (1992) In "Protein Pharmackinetics and Metabolism" (B.L. Ferraiolo et al, eds.) Plemeun Oress, New York, pp. 73–92.
Lamballe et al (1991) Cell 66: 967–979.
Ip et al (1992) Proc. Nat'l Acad. Sci. 89: 3060–3064.
Jessel et al. (1991) In "Principles of Neural Science" (E. Kandel et al, eds), Elsevier Science Publishing Co., Inc., New York, pp. 385–399.
Rosenberg et al (1989) J. Neurochem 48:865–875.
Kausel et al (1992) Neuroreport 3:885–888.
Litvinova et al (1991) Farmakol. Toksikol. (Moscow) 54(4):13–15.
Kita et al (1976) Folia Pharmacol. Japan 72:573–584. (See English Abstract).
Siuciak et al (1994) Brain Res. 633:326–330.
Siuciak et al (1993) Soc. Neurosci, Abstr. 19:663 (Abstr. #277.8).

*Primary Examiner*—Lila Peisee
*Assistant Examiner*—Nancy A. Johnson
*Attorney, Agent, or Firm*—Gail Kempler

[57] ABSTRACT

Infusions of brain-derived neurotrophic factor, neurotrophin-3 or neurotrophin-4 are used to produce analgesia in mammals. In addition, these neurotrophins are used to treat other diseases or disorders mediated by serotonin.

3 Claims, 4 Drawing Sheets

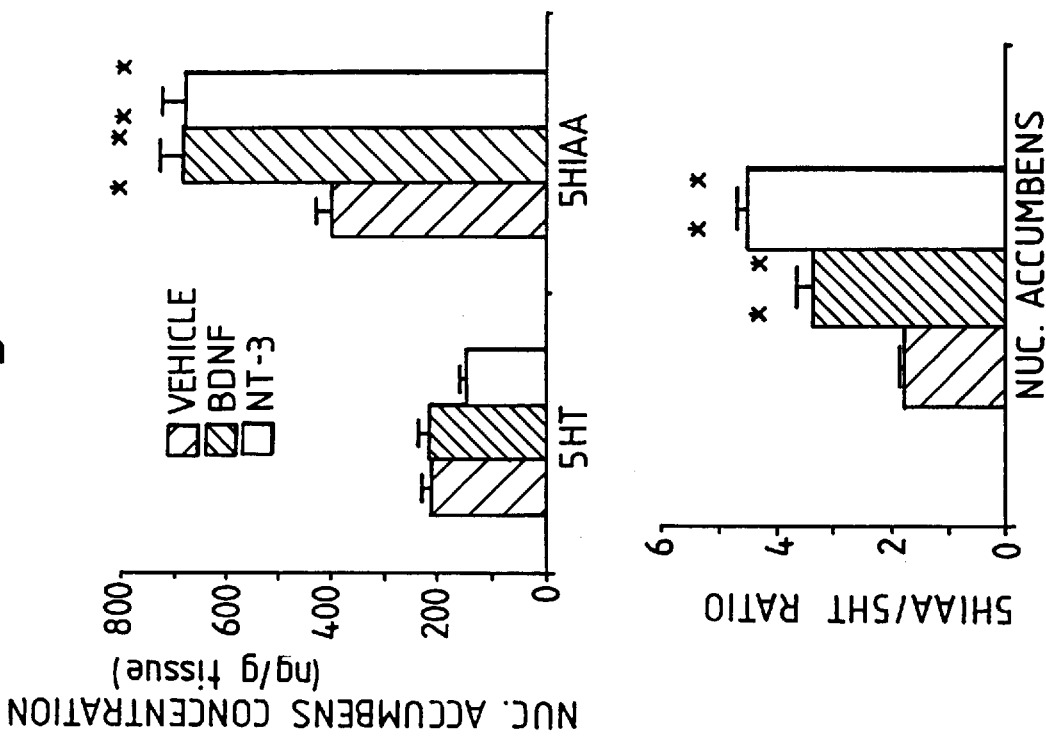
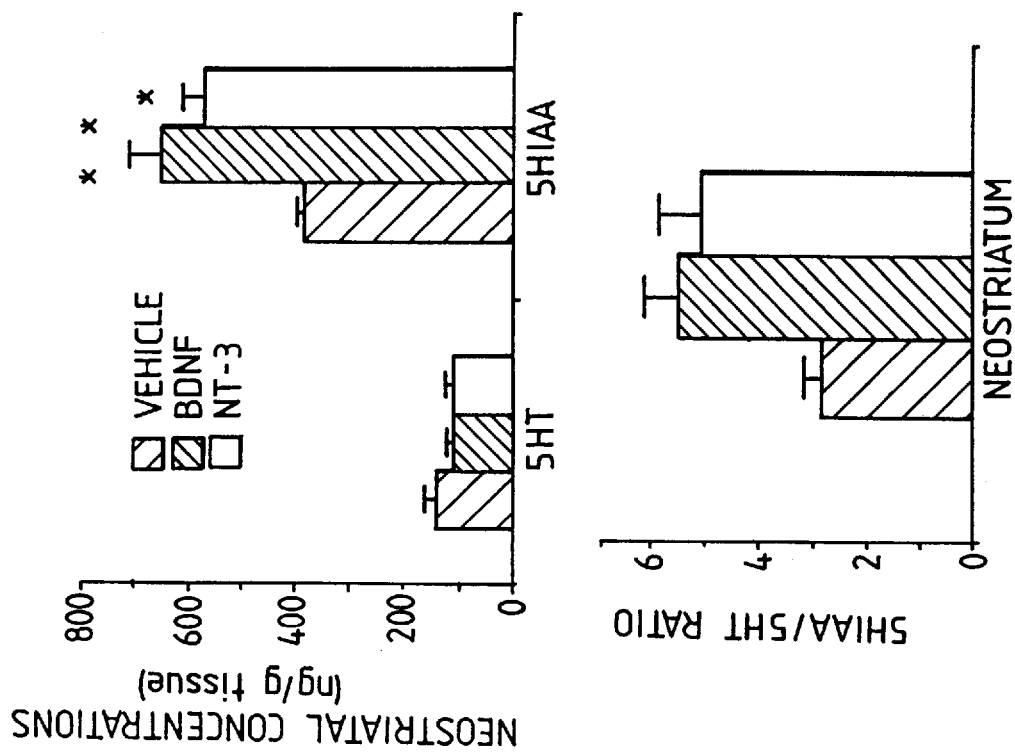

METHOD OF PRODUCING ANALGESIA USING NEUROTROPHINS

This is a division of application Ser. No. 08/110,399, filed Aug. 23, 1993, now abandoned, which is a continuation-in-part of U.S. application Ser. No. 07/944,823 filed Sep. 14, 1992 now abandoned which is incorporated in its entirety herein.

INTRODUCTION

Although drugs useful for the treatment of pain have been available to mankind since at least as early as the 3rd century B.C., the search continues for therapeutics that alleviate the sensation of pain without deleterious or undesirable side effects. As the sciences of molecular biology and neurobiology advance, rational drug design of such therapeutics becomes a realistic possibility.

Pain Transmission and Analgesia

In mammals, the receptors that respond selectively to noxious stimuli are known as nociceptors. Two distinct sets of peripheral sensory neurons are primarily responsible for the sensation of pain. The first, Aδ nociceptive neurons, contain myelinated axons and are aroused primarily by noxious heat and mechanical stimuli. The second set of nociceptive neurons, which possess unmyelinated axons and are known as C fibers, are activated by high intensity, mechanical, chemical and thermal stimulation. Each of these sets of neurons have their cell bodies in the dorsal root ganglia. Their processes are pseudounipolar, with one axon that terminates in the periphery and one that terminates on neurons in the dorsal horn of the spinal cord.

Analgesia is the loss of sensitivity to pain without loss of consciousness. In recent years, the convergence of various lines of research involving stimulation-produced analgesia (SPA), as well as analgesia caused by exogenous opioids such as morphine and endogenous opioids, have resulted in a model which explains the mechanism whereby pain is inhibited. [For a comprehensive review, see Kelly, Dennis, (1985) "Central Representations Of Pain and Analgesia", in Principals of Neural Science, Kandel and Schwartz, eds].

The first means known to man for inducing analgesia was through the use of plant-derived opioid narcotics such as morphine. The recent characterization of postsynaptic opioid receptors has lead to the discovery of naturally occurring, endogenous opioids which similarly bind the opioid receptor and thereby produce analgesia. The endogenous opioids include the met- and leu-enkephalins, as well as β-endorphin.

Analgesia can also be produced by electrical stimulation of the gray matter that surrounds the third ventricle, cerebral aqueduct, and fourth ventricle, in particular, the raphe nuclei or the periaqueductal gray region of the brain. Such stimulation results in complete and fairly long lasting analgesia. Stimulation induced analgesia is not increased by destruction of the periaqueductal gray, indicating that this region is not responsible for pain relay, but rather its effect is through active involvement in the inhibition of afferent input in the dorsal horn of the spinal cord and the trigeminal nerve nucleus. In fact, electrical stimulation appears to exert inhibition on spinal cord sensory neurons in a manner which is very similar to that observed using opioid peptides. The narcotic antagonist naloxone blocks both morphine and stimulation induced analgesia.

The monoamine neurotransmitter serotonin (5 hydroxytryptamine; 5HT) appears to be the common link in the analgesic mechanism in stimulation—as well as both endogenously—and exogenously-induced opioid analgesia. Depletion of serotonin by agents which block its synthesis, or by lesions of the serotonin-rich dorsal raphe nuclei, block the ability of both electrical stimulation and narcotics to diminish pain. Neurons in the periventricular and periaqueductal gray matter excite those in the raphe nuclei in the medullary reticular formation. Serotonergic fibers descend in the dorsolateral funiculus of the spinal cord to terminate in the substantia gelatinosa, where they are believed to activate enkephalinergic inhibitor neurons. Stimulation of C-fiber primary afferent neurons associated with pain results in the release of the potent neuropeptides substance P, calcitonin, gene related peptide (CGRP) and somatostatin, as well as the "fast" neurotransmitter glutamate. The activated enkephalinergic inhibitory neurons in turn exert presynaptic inhibitory control over the release of these neurotransmitters, thus blocking the sensation of pain.

Despite the initial, intense analgesic effect of the opioids, the development of drug tolerance, as well as the development of dependence on such drugs, remains a major limitation to their use. In addition, they produce a wide variety of unwanted side effects, including respiratory depression and constipation.

Non-steroidal anti-inflammatory drugs (NSAIDs) provide an alternative therapy for the treatment of pain. Their mode of action is believed to be through inhibition of cyclooxygenase, the enzyme responsible for biosynthesis of the prostaglandins.

As analgesics, the NSAIDs lack many of the side effects on the CNS that are associated with the opioids and they do not result in the development of dependence. They are only effective, however, on low to moderate intensity pain, and are not generally useful for intense pain. In addition, they have undesirable side effects, including the propensity to induce gastric or intestinal ulceration as well as disturbances of platelet function.

Despite the wide range of analgesic substances available, still lacking are drugs that are effective without undesirable side effects.

The Neurotrophins

Brain-derived neurotrophic factor (BDNF); [Barde, et al. Prog. Brain Res 71:185–189, (1987); Leibrock, et al., Nature 341: 149–152 (1989)], neurotrophin-3 (NT-3); [Maisonpierre, et al., Science, 247: 1446–1451, (1990)] and NT-4 [Ip, ,et al., Proc. Natl. Acad. Sci., U.S.A., 89: 3060–3064 (1992)] each potentiate the in vitro survival or phenotypic expression of distinct classes of neurons including central cholinergic [Alderson, et al., Neuron 5: 297–306, (1990)], dopaminergic [Hyman, et al., Nature 350: 230–232, (1991a); Kunsel, et al., (1991)], and GABAergic neurons [Hyman, et al., Soc. Neurosci. Ab. 17: 908, (1991b)].

Studies involving the in vivo actions of the neurotrophins, in particular the neurotrophin BDNF, have confirmed their actions in maintaining the survival and regulating the function or phenotype of various neuronal cells. Chronic intraseptal infusions of BDNF can prevent most of the axotomy-induced loss of cholinergic neuron staining in the medial septum [Morse et al, J. Neuroscience 13:4146–4156 (1993)]. In otherwise intact rats, chronic infusions of BDNF above the substantia nigra produces marked behavioral responses and elevated dopamine metabolism, the latter determined by increases in homovanillic acid (a breakdown product of dopamine; HVA) in the ipsilateral caudateputamen and even larger elevations in the dihydroxyphenylacetic/dopamine and HVA/dopamine ratios [Altar, et al., Proc. Natl. Acad. Sci., (USA) (89:11347–11351 (1992)].

High affinity binding sites for [125I]NT-3 are found within the medial substantia nigra and ventral tegmental area, nucleus accumbens, caudate-putamen, and raphe nuclei, and the binding to these sites is potently displaced by BDNF [Altar, et al., Am. Acad. Neurol. San Diego, Calif., (1992)]. BDNF mRNA is also present in these areas and appears to overlap with tyrosine hydroxylase (TOH)-positive cells [Gall, et al., (1992), unpublished observations]. Intrastriatal injections of [125I]-labeled NT-3 or BDNF result in a retrograde transport and accumulation of radioactivity within TOH-positive cells in these same regions [Wiegand, et al., Soc. Neurosci. AB., 17: 1121, (1991)]. In brain sections, NT-4 binding has been found to be widely distributed throughout the brain including the cortex, striatum, hippocampus, cerebellum, olfactory bulbs, periaqueductal gray, and raphe nuclei.

Based on the in vitro activities as well as in vivo binding data, it is expected that the actions of BDNF, NT-3 and NT-4 will extend to brain regions containing or innervated by these neurons.

SUMMARY OF THE INVENTION

In general, the invention features a method of providing analgesia by delivering cytokines, preferably neurotrophins, into a mammal to alleviate pain.

The invention also features a method of treating diseases or disorders that involve serotonin, whereby cytokines, preferably neurotrophins, are used to augment serotonin turnover in the brain and spinal cord.

In a preferred embodiment, brain-derived neurotrophic factor (BDNF) is delivered in the vicinity of the raphe nuclei or periaqueductal gray region of the midbrain of a mammal to inhibit pain.

BRIEF DESCRIPTION OF THE FIGURES

FIGS. 3A and 3B. Serotonin (5HT) and 5-hydroxyindole-acetic acid (5HIAA) concentrations and the 5HIAA/5HT ratio in the neostriatum (FIG. 3A) and nucleus accumbens (FIG. 3B) following 18 days of continuous bilateral supranigral infusions of vehicle, BDNF or NT-3 (12 $\mu$g/day). *$p<0.05$ and **$p<0.01$ vs vehicle, Dunnett's t-test. n=2–7 per group.

DETAILED DESCRIPTION OF THE INVENTION

Figure 1:
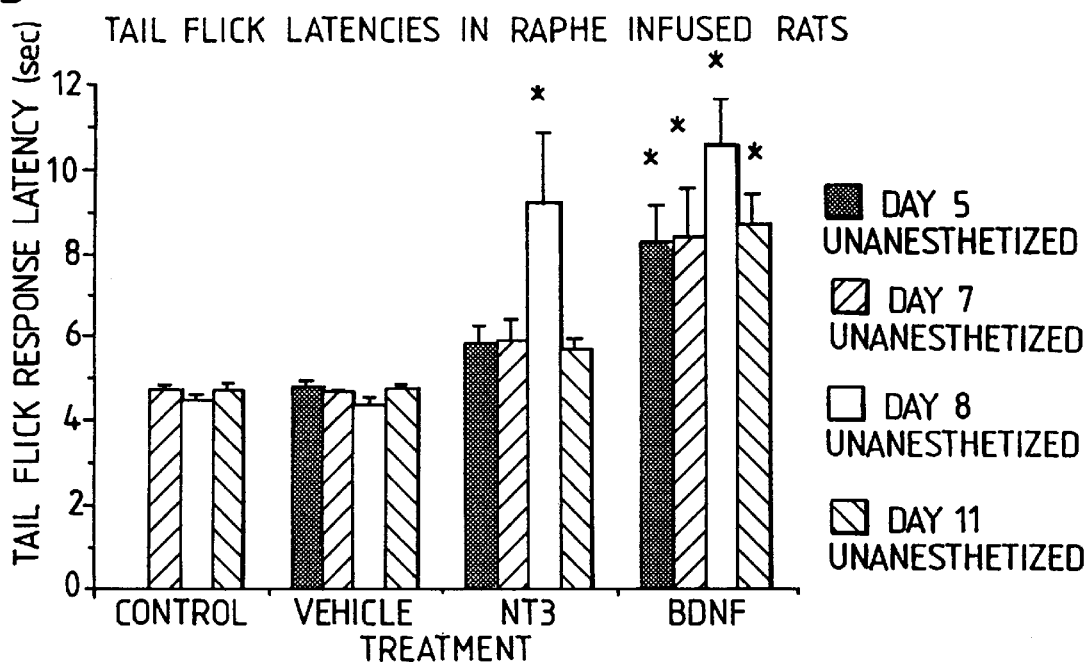
FIG. 1. Tail flick latencies of unoperated rats (control) or rats infused for 5, 7, 8, or 11 days with BDNF or NT-3 (12 $\mu$g/day) or PBS vehicle (12 $\mu$l/day) in the midbrain near the perlaqueductal gray/dorsal raphe (PAG/DR). Values are mean±sem, n=6–8/group. Day 8 anesthesia was obtained with metofane inhalation.

The present invention relates to a method of producing analgesia in mammals by administering a therapeutically effective dose of a neurotrophin. It is based, in part, on the discovery by applicants that neurotrophins, in particular the neurotrophins BDNF, NT-3 and NT-4 can induce analgesia when delivered in the vicinity of the raphe nuclei or periaqueductal gray of the brain.

The neurotrophin family includes brain-derived neurotrophic factor (BDNF), neurotrophin-3 (NT-3) and neurotrophin-4 (NT-4), all of which have recently been molecularly cloned and shown to be members of the nerve growth factor (NGF) family by virtue of their sequence homology [Leibrock, et al., Nature 341: 149–152, (1989); Hohn, et al., Nature, 344: 339–341, (1990); Maisonpierre, et al., Science, 247: 1446–1451, (1990a); Rosenthal, et al., Neuron, 4: 767–773, (1990); Ernfors, et al., Proc. Natl. Acad. Sci., U.S.A., 87: 5454–5458 (1990); Jones, et al., Proc. Natl. Acad. Sci. U.S.A., 87:8060–8064 (1990); Hallbook, et al., Neuron 6: 845–858, (1991); Ip, et al., Proc. Natl. Acad. Sci., U.S.A., 89: 3060–3064 (1992)]. This family of proteins plays an important role in both the developing and the adult vertebrate nervous system, where these proteins support neuronal survival, and regulate neuronal function such as neurotransmitter synthesis.

The cytokines which are useful in practicing the present invention include, but are not limited to, those neurotrophins that bind to the trkB or the trkC receptor. Definitive studies have indicated that BDNF and NT-4 primarily use the trkB receptor [Squinto, et al., Cell 65: 885–893 (1991); Ip, et al., Proc. Natl. Acad. Sci., U.S.A., 89: 3060–3064 (1992)] and NT-3 is the preferred ligand for trkC [Lamballe, et al., Cell 66: 967–979 (1991)]. In addition to the native neurotrophins, it is further contemplated that chimeras, or peptides or fragments derived from the neurotrophins, or any small molecules which act as trkB or trkC agonists will be useful to practice the present invention. Also useful would be any small molecule that can activate at any point the signal transduction pathway of a neurotrophin.

For example, neurotrophins useful for practicing the present invention may be prepared by first cloning and sequencing a gene encoding each respective protein. Each cloned gene may then be expressed in a prokaryotic or eukaryotic expression system. Any of a number of protocols available to one skilled in the art may be utilized to clone and sequence the neurotrophins. The recombinant neurotrophin gene may be expressed and purified utilizing any number of methods. In a preferred, nonlimiting embodiment of the invention, each factor may be prepared from bacterial cells or eukaryotic cells that express recombinant factor. The gene encoding the factor may be subcloned into a bacterial expression vector, such as for example, but not by way of limitation, pCP110.

The recombinant factors may be purified by any technique which allows for the subsequent formation of a stable, biologically active protein. For example, and not by way of limitation, the factors produced in prokaryotes may be recovered from cells as inclusion bodies, followed by quantitative extraction in 8M guanadinium chloride and dialysis. In order to further purify the factors, conventional ion exchange chromatography, hydrophobic interaction chromatography, reverse phase chromatography or gel filtration may be used.

The active ingredient, which may comprise one purified neurotrophin, or a hybrid, peptide fragment or mutant thereof, a combination of several neurotrophins, or a combination of neurotrophin and opioid peptide, should be formulated in a suitable pharmaceutical carrier for administration in vivo by any appropriate route including, but not limited to injection (e.g., intravenous, intraperitoneal, intraparenchymal, intramuscular, subcutaneous, endoneural, perineural, intraspinal, intracerebroventricular, intrathecal etc.), by absorption through epithelial or mucocutaneous linings (e.g., oral mucosa, rectal and intestinal mucosa, etc.); or by a sustained release implant, including a cellular or tissue implant.

The concentration of the active ingredient used in the formulation will depend upon the effective dose required and the mode of administration used. The dose used should be sufficient to achieve circulating plasma concentrations of active ingredient that are efficacious. Effective doses may be extrapolated from dose-response curves derived from in vitro or animal model test systems.

In a preferred embodiment, neurotrophins are delivered in the vicinity of the raphe nuclei or periaqueductal gray. The raphe nuclei include any of the midline group of neurons that are associated with the midsagittal seam of the brain stem. A characteristic feature of the raphe nuclei, which include the caudal linear nucleus, the dorsal raphe nucleus, the median raphe nucleus, the raphe pontis nucleus, the raphe magnus nucleus, the raphe obscurus nucleus, and the raphe pallidus nucleus, is their high proportion of serotonergic neurons.

In another embodiment, neurotrophins are delivered along the ascending and descending projections of the serotonergic neurons of the raphe nuclei, including, but not limited to the thalamus, hypothalamus and epithalamus, the basal telencephalon, the cerebral cortex, the brain stem, cerebellar projections and spinal projections.

In a preferred embodiment, neurotrophins, such as BDNF, are delivered to the dorsal horn of the spinal cord, a descending projection of the raphe nuclei associated with pain. As described herein in Example 2, infusions of neurotrophins such as, for example, BDNF, cause an alteration in the level of serotonin in the spinal cord. Infusion of such neurotrophins directly into the spinal cord via, for example, intrathecal delivery, may provide an effective analgesic alternative to morphine without the concomitant side effects associated with the opioid analgesics.

In another embodiment, infusions are made into one of the main target areas of the ascending projections from the dorsal and median raphe nuclei, the hippocampus. This area receives afferents from both the dorsal and median raphe, and the smaller dorsal raphe projections reach the dentate gyrus through the entorhinal cortex and perforant path [Azmitia and Segal, J. Comp. Neurol. 179, 641–668 (1978)]. Projections from the median raphe to the hippocampal region are more numerous than from the dorsal raphe, and these median raphe projections reach the hippocampal region via two routes: the cingulum bundle, and the fornix [Azmitia and Segal, J. Comp. Neurol. 179, 641–668 (1978)]. Additional projections reach the hippocampus through the amygdala, which in turn receives its raphe projection through the ansa peduncularis-ventral amygdaloid bundle [Moore, in B. L. Jacobs and A. Gelperin (eds) Serotonin neurotransmission and behaviors, 35–71 (1981); Moore and Halaris, J. Comp. Neurol. 164: 171–184 (1975)].

Depending upon the mode of administration, the active ingredient may be formulated in a liquid carrier such as saline, incorporated into liposomes, microcapsules, polymer or wax-based and controlled release preparations, or formulated into tablet, pill or capsule forms. Alternatively, neurotrophins may be produced in situ by transfected cells which are implanted or infused into the target site.

Although not intending to be limited by theory, it is postulated that the analgesic properties of the neurotrophins described herein may be due to their ability to alter serotonin neurotransmission within the brain or spinal cord. This is based on the findings, by applicants, in studies in which changes in the levels of serotonin and its principle metabolite, 5-hydroxyindoleacetic acid (5HIAA), following infusions of BDNF and NT-3 in the vicinity of the raphe nuclei were monitored (see Examples 2 and 3 below). Such neurochemical data appears to confirm that infusions of BDNF and NT-3 in this area result in elevated levels and turnover of serotonin, which may subsequently effect release of enkephalin or other naturally occurring opioids, thus causing the analgesia observed following their infusion. Selective serotonin depletion studies have shown that serotonin mediates the analgesic property of morphine and that serotonin is required for normal pain sensitivity [for review, see Messing and Lytle, Pain 4: 1–21, (1977)]. Increases in serotonin turnover in such lesioned animals by precursor loading can restore pain thresholds to normal levels and potentiate the analgesic properties of morphine. Accordingly, intrathecal, intracerebroventricular or intraparencymal delivery of neurotrophin could substitute for intrathecal morphine or potentiate the analgesic effects of intrathecal morphine that is given to cancer patients.

The present invention further contemplates other uses of cytokines such as the neurotrophins for ameliorating or moderating diseases or disorders in which serotonin is believed to play a role. For example, serotonin has been implicated in autism, since some autistic patients show elevated platelet and plasma serotonin levels and show dramatic improvement when treated with the selective serotonin reuptake blocker fenfluramine [Ritvo, et al., Psychopharmacol. Bull 22: 133–140 (1986)]. Interestingly, human platelets contain BDNF [Yamamoto, et al., J. Neurosci. 10: 3469–3477 (1990)], which could modulate serotonin metabolism in these cells. If platelets contain a sequestration mechanism for BDNF, intravenous infusions of BDNF could potentially benefit autistic children via effects on serotonin in the absence or presence of fenfluramine. Serotonin can also modulate animal models of anxiety [Iversen, Neuropharmacol 23: 1553–1560 (1984)], hyperactivity [Fink, et al., Eur. J. Pharmacol. 75: 289–296 (1981); Callaway, et al., J. Pharmacol. and Exper. Therapeutics 254: 456–464 (1990)], and anorexia [Parada, et al., Brain Res. 577: 218–115 (1992)]. Thus BDNF could ameliorate anxiety, hyperactivity syndromes, or obesity through its effects on serotonin.

EXAMPLE 1

The Neurotrophins Have a Potent Analgesic Effect

Materials and Methods

Production and Purity of BDNF, NT-3 and NT-4. Recombinant human BDNF [Leibrock, et al., Nature 341:149–152

(1989)] was produced by expression of the gene, complete with its precursor sequence, in Chinese hamster ovary (CHO) cells grown in serum free media. The recombinant human BDNF was at least as active as BDNF isolated from pig brain using bioassays of cultured dorsal root ganglion explants or dissociated neurons (Y. Barde, personal communication). Recombinant human NT-3 (119 amino acid residues) was produced in CHO cells as described [Radziejewski, et al., Biochemistry 31: 4431–4436 (1992)]. The eluted material was monitored for protein content by amino acid analysis and found to be >95% NT-3 protein, of which 50% was comprised of intact protein and 50% of cleaved product in which the 5N-terminal amino acids were missing. BDNF and NT-3 was monitored for biological activity using dissociated lumbar dorsal root ganglia (DRG) cells from E8 chicken embryos maintained 2 days in vitro [Lindsay, et al., Neurosci. 12: 45–51 (1984)]. BDNF and NT-3 each mediated survival of 30% and 35% subpopulations, respectively, of DRG neurons with $EC_{50}$ values of approximately 0.01–0.1 ng/ml. NT-4 can be produced in CHO cells and assayed as set forth in Ip, et al., Proc. Natl. Acad. Sci. USA 89:3060–3064 (1992) or be produced in E. coli (see Panayotatos and Fandl, PCT application WO/92/22665 published on Dec. 23, 1992). NT-4 produced and purified from E. coli showed greater than 95% purity and, like NT-4 which was produced in CHO cells, promoted the survival in serum free medium of MG87 fibroblasts that express the rat TrkB receptor and the survival and neurite growth of rat E15/16 DRG cells.

Formulation, Stability, and Delivery of BDNF and NT-3 from Osmotic Pumps. Each factor was diluted in PBS to 1.0 mg/ml (BDNF) or 0.5 mg/ml (NT-3,) and loaded into Alzet 2002 osmotic pumps (Alza Corp., Palo Alto, Calif.; flow rate 0.5 μl/hr). Each pump was connected to 11.2 cm of vinyl tubing (Biolab Products, Lake Havasu City, Ariz.) filled with the same solution contained in the pumps, immersed in a glass vial that contained PBS and 0.002% sodium azide and maintained at 37° C. for 2 weeks. The effluent was collected into siliconized 1.5 ml polypropylene tubes that contained 400 μl PBS. The collection tubes were replaced with new tubes every 4 days, and the aliquots were measured for biological activity using the dorsal root ganglia outgrowth assay. Both factors retained full biological activity over the 14 days compared to the activity obtained with the same material stored at 2° C.

Animal Surgery. Male Sprague-Dawley rats (200–240 g; n=6–12/group) were housed and treated in compliance with AALAC guidelines. One day prior to surgery, the flow moderators of the osmotic pumps were fitted with a 2 cm piece of silated PE50 tubing (Micro-Renathane, Braintree Scientific, Braintree, Mass.) and a 28G osmotic pump connector cannula (Plastics One, Inc., Roanoke, Va.) that was 5.5, 6.0, and 6.8 mm long for intrastriatal, intra-accumbens and supranigral, or raphe infusions, respectively. The pumps and flow moderators were filled with vehicle (sterile PBS), NT-3 or BDNF at a concentration of 1 mg/ml to deliver 12 μg of either factor each day. All tubing joints were sealed with cyanoacrylate adhesive (Wonder Bond Plus, Borden, Inc., Columbus, Ohio) and the flow moderator was sealed to the pump with melted dental wax. Each rat was anesthetized with an i.p. injection of chloropent (149 mg/kg chlorohydrate and 30.8 mg/kg sodium pentobarbital) and mounted in a small animal stereotaxic apparatus (Kopf, Tijunga, Calif.). A 2 cm long incision was made on the scalp, through which the osmotic pump was inserted and subcutaneously implanted between the shoulder blades. A 1 mm diameter hole was drilled in the calvarium either above the center of either the right caudate-putamen [at the skull surface co-ordinates: anterior 0.3 mm; lateral±3.0 mm], left and right nucleus accumbens [anterior 1.0 mm; lateral±2.0 mm], above left and right substantia nigra [at the interaural co-ordinates: anterior 2.5 mm; lateral from midline±2.7 mm], in the midbrain, adjacent to the periaqueductal grey and dorsal raphe nuclei [7.6 mm posterior to bregma, 1 mm lateral to the sagittal suture] or intracerebral ventricular (i.c.v.) infusion aimed at the lateral ventricle [0.4 mm posterior to bregma, 1.8 mm lateral to the sagittal suture]. Either cannula system was inserted through the skull hole, attached to the skull with cyanoacrylate adhesive, and the scalp incision was closed with wound clips. Several animals sacrificed for histological verification of cannula placement following injection of 1.5 μl of dye revealed cannula terminations mostly above the middle or medial aspect of the pars compacta, in the central caudate-putamen, in the nucleus accumbens just dorsal to the anterior commissure, or about 0.5 mm ventral to the midpoint between the medial and dorsal raphe nuclei. Verification of cannula placements in experimental animals took place at the time of sacrifice. Animals with incorrect cannula placements were removed from the study and the data was not used for statistical analysis.

Analgesiometric Test. The tail flick test follows the procedure derived from [D'Amour and Smith, J. Pharmacol. Exp. Ther. 72: 74–79 (1941)]. A noxious stimulus, produced by a beam a high intensity light was focused on the tail. The response time was measured automatically and defined as the interval between the onset of the heat stimulus and the abrupt flick of the tail. The average of three consecutive determinations, taken in immediate succession, was taken as the tail flick response latency. In order to minimize possible tissue damage, a different patch of tail skin was stimulated on each trial. Animals not responding after 14 seconds were removed from the apparatus and assigned a response latency of 14 seconds.

Results

Tail flick latencies of unoperated rats (control) or rats infused for either 5, 7, 8, or 11 days with phosphate buffered saline vehicle or BDNF (12 ug/day) or NT-3 (12 ug/day) near the dorsal and median raphe nuclei are shown in FIG. 1. A one-way analysis of variance confirmed that there was a significant effect of treatment after 5 days of infusion of BDNF($F_{2,20}$=10, p<0.001). A post-hoc Dunnett's t test (t=4.3, k=3, df=19) revealed a significant analgesic effect of the BDNF-infused rats versus vehicle infused rats. Although the effect of the NT-3 infusion did not reach significance when using the post-hoc tests (Dunnett: t=1.4, k=3, df=21, p>0.05), a Student's t test comparing the vehicle and NT-3 infused groups showed a significant analgesic effect of the NT-3 treatment (NT-3 vs. VEH, df=14, t=2.32, p<0.046).

Tail flick testing for the BDNF or NT-3 treated animals was repeated on infusion day 7 with identical results (FIG. 1). At this time, an unoperated group of weight matched rats was also tested on the tail flick for comparison. A one-way ANOVA confirmed a significant effect of treatment ($F_{3,28}$= 8.8, p<0.001). No difference was found between the unoperated control or vehicle-infused rats (Dunnett: t<0.04, k=3, df=26). The BDNF infusion produced a significant level of analgesia (Dunnett: t=4.33, k=3, df=26; p<0.01) when compared to the control group. Again, the NT-3 tail flick response latencies did not reach significance in the post-hoc tests (Dunnett's: t=1.41, k=3, df=26, p>0.05) but did show a significant analgesic level when a Student's t test was used for comparison (NT-3 vs. VEH, t=2.25, df=14, p<0.04). A two-way ANOVA comparing tail flick response latencies on day 5 and 7 of infusion again indicated a significant effect of treatment ($F_{2,41}=16.9$, $p<0.001$). However, there was no decrease in response latencies between infusion days, suggesting no development of tolerance ($F_{1,41}=0.037$, $p=0.85$, non-significant).

Figure 2:
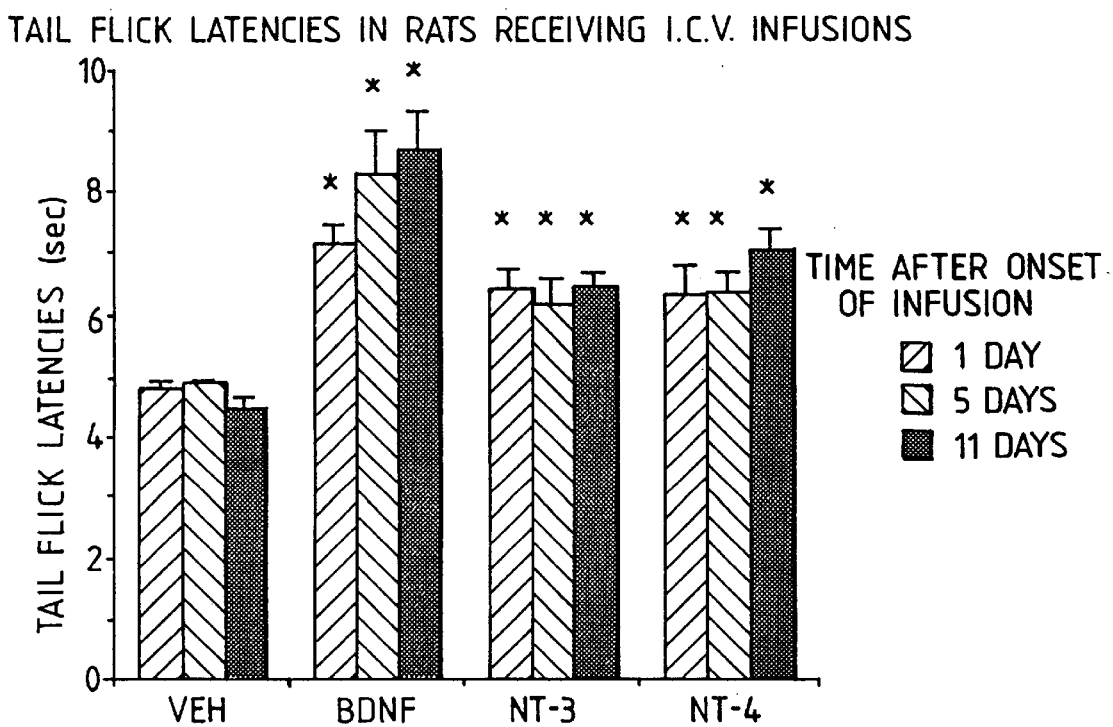
FIG. 2: Tail flick latencies of rats receiving introcerebral-ventrigular (i.c.v.) infusions of PBS vehicle (12 $\mu$l/day) or BDNF (24 $\mu$g/day), NT-3 (24 $\mu$g/day) or NT-4 (11.5 $\mu$g/day) for 1, 5 or 11 days. Values shown are mean±SEM for 7–8 rats per group.

Tail flick latencies of rats infused for either 1, 5, or 11 days with phosphate buffered saline vehicle or neurotrophin (BDNF or NT-3=24 µg/day or NT-4=11.5 µg/day) into the lateral ventricle are shown in FIG. 2. A one-way ANOVA showed a significant effect of treatment after only 1 day of infusion for all three neurotrophins ($F_{3,30}=9.7$, $p<0.001$). A post-hoc Dunnett's t test revealed a significant analgesic effect of the BDNF ($t=5.1$, $p<0.01$), NT-3 ($t=3.5$, $p<0.01$) and NT-4 ($t=3.4$, $0<0.01$) rats versus vehicle infused rats. Tail flick testing was repeated 5 days after the onset of infusion. Again a significant effect of treatment was seen ($F_{3,29}=7.3$, $p<0.001$). Again, post-hoc tests indicated that BDNF, NT-3 and NT-4 infusions produced a significant analgesic effect. Identical results were found 11 days after the onset of infusion ($F_{3,30}=19.0$, $p<0.001$) with BDNF, NT-3 and NT-4 infusions all significantly elevating the tail flick latency.

A two-way ANOVA comparing tail flick response latencies on days 1, 5 and 11 again indicated a significant effect of treatment ($F_{3,91}=31.9$, $p<0.001$). No significant change in response latencies between infusion days was found suggesting a maximum effect was achieved by day 1, and no tolerance was observed ($F_{2,91}=1.5$, $p=0.2$, not significant).

It has been clearly demonstrated that the tail flick response can be modulated by activation of pathways descending from the brain to the spinal cord [for reviews see Willis, et al., Sensory Mechanisms of the Spinal Cord, R. E., Plenum Press, New York (1978); Yaksh, *Spinal Afferent Processing,* Plenum Press, New York (1986)]. For this reason, the tail flick test is often used to assay the effectiveness of various agents which require spinal and/or supraspinal structures for their expression. Several investigators have observed the tail flick reflex in anesthetized rats [Banks, et al., Phar. Biochem. Behav. 31: 397–403 (1988); Brink, et al., Brain Behav. Evol. 17: 1–47 (1980); Grossman, et al., J. Comp. Neurol. 206: 9–16 (1982); Sandkuhler, et al., Brain Research 305: 67–77, p. 77–87 (1984); Zorman et al., Brain Research 236: 77–84 (1981)]. Tail flick testing on infusion day 8 was performed in metofane-anesthetized rats. A one-way ANOVA indicated a significant effect of treatment ($F_{3,28}=19.49$, $p<0.001$). Post-hoc tests found no difference between unoperated control and vehicle-infused rats (Dunnett: k=4, df=28, t=0.09, non-significant). However, significant antinociceptive effects of both NT-3 (Dunnett: t=5.69, $p<0.01$); and BDNF (Dunnett: t=5.1, $p<0.01$) were seen. A two-way ANOVA comparing tail flick response latencies on day 7 (unanesthetized) and 8 (anesthetized) of infusion again indicated a significant effect of treatment ($F_{3,57}=26.8$, $p<0.001$). Post-hoc comparisons found a significant difference in response latencies between the awake and metofane-anesthetized rats ($F_{3,57}=4$, $p<0.046$) but no changes between anesthetized rats in the control and vehicle-infusion groups. Although increased tail flick response latencies were observed for both the BDNF (day 7: 8.3±1.1 sec vs. day 8: 10.5±1.1) and NT-3 (day 7: 5.9±0.53 sec vs. day 8: 9.2±1.7 sec) infused groups, post-hoc comparisons indicated only the antinociceptive effect of NT-3-infusion was significantly different between awake and anesthetized animals.

Tail flick testing in unanesthetized rats was repeated on infusion day 11 with identical results to both days 5 and 7. A one-way ANOVA confirmed a significant effect of treatment ($F_{3,28}=27.4$, $p<0.001$). No difference was found between the unoperated control or vehicle infused rats (Dunnett: t=0.05, k=4, df=26). BDNF infusion produced a significant level of analgesia (Dunnett: t=7.7, k=4, df=28, $p<0.01$) when compared to the control group. The tail flick response latencies of the NT-3-infused rats also reached significance in the post-hoc tests (Dunnett: t=2.5, k=4, df=26, $p<0.05$). A two-way ANOVA comparing tail flick response latencies on day 5 and 11 of infusion again indicated a significant effect of treatment ($F_{2,41}=31.39$, $p<0.001$). Again, there was no difference in response latencies between infusion days, suggesting no development of tolerance ($F_{1,41}=0.012$, $p=0.91$, non-significant).

The midbrain and i.c.v. infusion paradigms show several distinct differences. First, NT-3 infusion in the lateral ventricle results in analgesia as early as 24 hours after the onset of infusion, whereas midbrain infusion of NT-3 has never shown significant increases in tail flick latencies this soon. Secondly, all neurotrophins reached their maximum analgesic effect by day 1, i.e. day 1=day 5 tail flick latencies, following i.c.v. infusion. Following midbrain infusion, day 5 tail flick latencies were consistently and significantly higher than day 1. Finally, the analgesia obtained from midbrain infusions was greater than that seen following i.c.v. infusion, despite the fact that the concentration used was lower (midbrain infusions used 12 ug/day, while the i.c.v. experiments used 24 ug/day for BDNF and NT-3).

EXAMPLE 2

The Neurotrophins Alter Serotonin Levels in the Dorsal and Median Raphe Nucleus, Hippocampus and Spinal Cord Materials and Methods Animal Surgery. Animal surgery was performed as in Example 1.

Neurochemical Measurements. All reagents were obtained from Sigma Chemical Co. (St. Louis, Mo.) unless indicated. At 15 to 17 days after the surgery, the animals were sacrificed and the brains removed. The dorsal and median raphe nucleus were dissected and homogenized in 10 volumes of 0.32M sucrose. For neurochemical analysis of the spinal cord, a 4 mm segment through the center of the lumbar enlargement was used. A 45 µl aliquot for indoleamine determinations was added to 5 µl of a 4N perchlorate, 1 mM ascorbate, 3 µg/ml dihydroxybenzylamine (DHBA) internal standard solution. The samples were stored frozen until assay. The remainder of the samples were divided into 3 aliquots and frozen at −70° C. Protein determinations were carried out using one of these aliquots according to the method of Smith, et al., [Anal. Biochem., 76–85 (1985)].

Indoleamine Determinations. Serotonin (5HT) and its principle metabolite, 5-hydroxyindole-acetic acid (5HIAA), were measured using an isocratic HPLC elution system and electrochemical detection, using a 16 channel coulometric array detector (ESA, Inc., Bedford, Mass.); [Gamache, et al., J. Chromatographic Methods 635:143–150 (1993)].

Results

Serotonin Levels in the Dorsal and Median Raphe Nucleus

Measurements of 5HT and 5HIAA levels in the dorsal and median raphe of unoperated rats (control) or rats infused for 14 days with either phosphate buffered saline vehicle or neurotrophin into the midbrain near the PAG/DR (BDNF or NT-3, 12 ug/day) are shown in Table 1. A one-way ANOVA showed a significant effect of treatment in 5HT ($F_{3,26}=5.6$, $p<0.005$), 5HIAA ($F_{3,26}=8.8$, $p<0.001$) levels, as well as in the 5HIAA/5HT ratio (df=3,26, F=7.3, $p<0.001$). Post-hoc comparisons showed significant increases in both 5HT and 5HIAA in the BDNF treated group. The 5HIAA/5HT ratio was elevated in both the BDNF (Dunnett's: t=4.0, k=4, df=24, $p<0.05$) and NT-3 (Dunnett's: t=3.8, k=4, df=24, $p<0.05$) infusion groups.

TABLE 1

5HT AND 5HIAA CONCENTRATIONS AND THE 5HIAA/5HT RATIO IN DORSAL AND MEDIAN RAPHE MICROPUNCHES.

| GROUP | 5HT | 5HIAA | 5HIAA/5HT |
|---|---|---|---|
| Unoperated Controls | 8.5 ± 0.41 (8) | 7.9 ± 0.70 (8) | 0.92 ± 0.05 (8) |
| Vehicle-Infused | 10.4 ± 0.84 (7) | 8.5 ± 0.99 (7) | 0.81 ± 0.06 (7) |
| BDNF-Infused | 12.9 ± 0.78* 23%↑(7) | 13.8 ± 0.79* 63%↑(7) | 1.07 ± 0.02* 32%↑(7) |
| NT-3-infused | 9.5 ± 1.11 (6) | 10.0 ± 1.17 (6) | 1.06 ± 0.04* 31%↑(6) |

5HT and 5HIAA concentrations and the 5HIAA/5HT ratio in dorsal and median raphe micropunches in unoperated rats (control) or in rats which received 14 days of continuous infusion of PBS vehicle or neurotrophin (BDNF or NT-3, 12 ug/day). Values are mean ± sem. Number of animals is shown in parentheses.
*p < 0.05 vs. vehicle.

Serotonin Levels in the Hippocampus

Measurements of 5HT and 5HIAA levels in the hippocampus taken from unoperated rats (control) or rats infused for 14 days with either phosphate buffered saline vehicle or neurotrophin (BDNF or NT-3, 12 ug/day) in the midbrain near the PAG/DR are shown in Table 2. A one-way ANOVA showed no significant effect of treatment in 5HT levels ($F_{3,28}=0.87$, p=0.47). However, a one-way ANOVA did indicate a significant effect of treatment in both the 5HIAA levels ($F_{3,28}=9.7$, $p<0.001$), as well as in the 5HIAA/5HT ratio (df=3,28, F=8.8, $p<0.001$). Post-hoc comparisons showed significant increases in both 5HIAA (Dunnett's t: k=4, df=26, t=4.5, $p<0.01$) and 5HIAA/5HT ratio (Dunnett t: k=4, df=26, t=4.6, $p<0.01$) in the BDNF-infused group versus the vehicle-infused group.

TABLE 2

5HT AND 5HIAA CONCENTRATIONS AND THE 5HIAA/5HT RATIO IN THE HIPPOCAMPUS FOLLOWING DORSAL AND MEDIAN RAPHE INFUSION.

| TREATMENT | 5HT pg/ug protein | 5HIAA pg/ug protein | 5HIAA/5HT ratio |
|---|---|---|---|
| VEHICLE-INFUSED | 2.6 ± 0.2 (8) | 2.4 ± 0.2 (8) | 0.98 ± 0.07 (8) |
| BDNF-INFUSED | 2.6 ± 0.2 (7) | 4.0 ± 0.4* 67%↑(7) | 1.59 ± 0.15* 62%↑(7) |
| NT-3-INFUSED | 2.4 ± 0.2 (6) | 2.5 ± 0.2 (6) | 1.05 ± 0.06 (6) |
| UNOPERATED CONTROLS | 2.2 ± 0.2 (8) | 2.4 ± 0.2 (8) | 1.09 ± 0.06 (8) |

5HT and 5HIAA concentrations and the 5HIAA/5HT ratio in the hippocampus of unoperated rats (control) or in rats which received 14 days of continuous infusion of PBS vehicle or neurotrophin (BDNF or NT-3, 12 ug/day) near the dorsal and median raphe nuclei. Values shown are mean ± sem. Number of animals is shown in parentheses.
*p < 0.05 vs. vehicle.

Serotonin Levels in the Spinal Cord

Measurements of 5HT and 5HIAA levels in the lumbar spinal cord taken from rats infused for 14 days with either phosphate buffered saline vehicle or neurotrophin (BDNF or NT-3, 12 ug/day) in the midbrain near the PAG/DR are shown in Table 3. A one-way ANOVA showed no significant effect of treatment in 5HT levels ($F_{3,28}=0.71$, p=0.56). However, a one-way ANOVA did indicate a significant effect of treatment in both the 5HIAA levels ($F_{3,28}=3.7$, $p<0.03$), as well as in the 5HIAA/5HT ratio ($F_{3,28}=10.3$, $p<0.001$). Post-hoc comparisons showed significant increases in both 5HIAA (Dunnett t: k=4, df=26, t=3.7, $p<0.01$) and 5HIAA/5HT ratio (Dunnett t: k=4, df=26, t=5.0, $p<0.01$) in the BDNF-infused group versus the vehicle-infused group.

TABLE 3

5HT AND 5HIAA CONCENTRATIONS AND THE 5HIAA/5HT RATIO IN THE LUMBAR SPINAL CORD FOLLOWING DORSAL AND MEDIAN RAPHE INFUSION.

| TREATMENT | 5HT pg/ug protein | 5HIAA pg/ug protein | 5HIAA/5HT ratio |
|---|---|---|---|
| VEHICLE-INFUSED | 8.1 ± 0.8 (8) | 4.0 ± 0.5 (8) | 0.49 ± 0.03 (8) |
| BDNF-INFUSED | 9.9 ± 0.8 22%↑(7) | 7..0 ± 0.6 75%↑(7) | 0.71 ± 0.04 45%↑(7) |
| NT-3-INFUSED | 9.2 ± 1.0 (7) | 5.0 ± 0.5 (7) | 0.55 ± 0.03 (7) |

5HT and 5HIAA concentrations and the 5HIAA/5HT ratio in the lumbar spinal cord of rats which received 14 days of continuous infusion of PBS vehicle or neurotrophin (BDNF or NT-3, 12 ug/day) near the dorsal and median raphe nuclei. Values shown are mean ± sem. Number of animals is shown in parentheses.
*p < 0.05 vs. vehicle.

Serotonin Levels in the PAG/DR or Lumbar Spinal Cord

Measurements of 5HT and 5HIAA levels in the periaqueductal gray/dorsal raphe (PAG/DR) or lumbar spinal cord of rats infused for 14 days with either phosphate buffered saline vehicle or NT-4, (11.5 ug/day) into the lateral ventricle (i.c.v.) are shown in Table 4. In the PAG/DR, NT-4 infusion resulted in a significant increase in 5HIAA levels (51%, t=2.3, df=9, $p<0.046$). Although not statistically significant, there was a trend towards an increase in 5HT levels (13%, t=1.9, df=9, $p<0.08$) as well the 5HIAA/5HT ratio (29%, t=1.8, df=9, $p<0.09$). In the lumbar spinal cord, NT-4 infusion significantly increased the concentrations of 5HT (60%, t=2.6, df=10, $p<0.025$) and its metabolite, 5HIAA (109%, t=3.2, df=10, $p<0.009$). Although not statistically significant, there was a 23% increase in the 5HIAA/5HT ratio (t=2.1, df=10, $p<0.061$).

TABLE 4

5HT and 5HIAA CONCENTRATIONS FOLLOWING I.C.V. INFUSION OF NT-4

| GROUP | 5HT pg/μg protein | 5HIAA pg/μg protein | 5HIAA/5HT ratio |
|---|---|---|---|
| Periaqueductal gray and Dorsal raphe | | | |
| Vehicle | 9.39 ± 0.4 | 6.8 ± 0.1 | 0.73 ± 0.03 |
| NT-4 | 10.7 ± 0.6 | *10.3 ± 2.1 | 0.95 ± 0.15 |
| Spinal Cord | | | |
| Vehicle | 10.9 ± 1.1 | 6.5 ± 0.5 | 0.62 ± 0.04 |
| NT-4 | *17.4 ± 2.7 | *13.6 ± 3.1 | 0.76 ± 0.05 |

5HT and 5HIAA concentrations and the 5HIAA/5HT ratio in the periaqueductal gray/dorsal raphe and lumbar spinal cord of rats which received 14 days of continuous infusion of PBS vehicle or NT-4 (11.5 ug/day) into the lateral ventricle. Values shown are mean ± sem, n = 4–8 rats/group.
*p < 0.05 vs. vehicle.

EXAMPLE 3

Effect of the Neurotrophins on Serotonin Levels in the Caudate Putamen and Nucleus Accumbens

Materials and Methods

Animal surgeries and neurochemical measurements were performed as set forth in Examples 1 and 2.

Results

Figure 4:
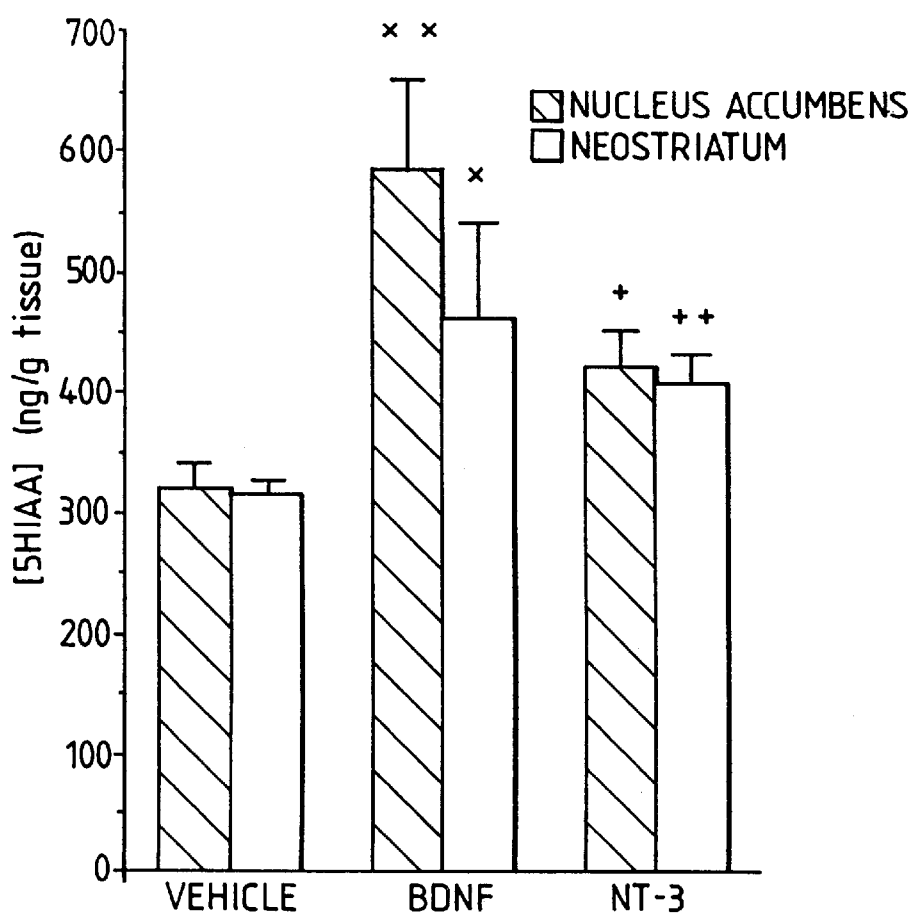
FIG. 4. Elevated 5HIAA concentrations in the nucleus accumbens and neostriatum following 18 days of continuous bilateral nucleus accumbens infusions of vehicle, BDNF or NT-3 (12 $\mu$g/day). *$p<0.05$ and **$p<0.01$ vs vehicle, Dunnett's t-test; +$p<0.05$, ++$p<0.02$ virus vehicle paired t-test. n=3–6 per group.

5HT and 5HIAA concentrations and the 5HIAA/5HT ratio in the neostriatum and nucleus accumbens were elevated consistently in the nucleus accumbens following 18 days of continuous bilateral supranigral infusion of BDNF or NT-3 (12 μg/day; FIGS. 3A and 3B). 5-HIAA levels were also elevated by bilateral infusion of BDNF or NT-3 into the nucleus accumbens (FIG. 4). Serotonin levels were undetectable in tissues obtained from animals receiving nucleus accumbens infusions.

Figure 5A:
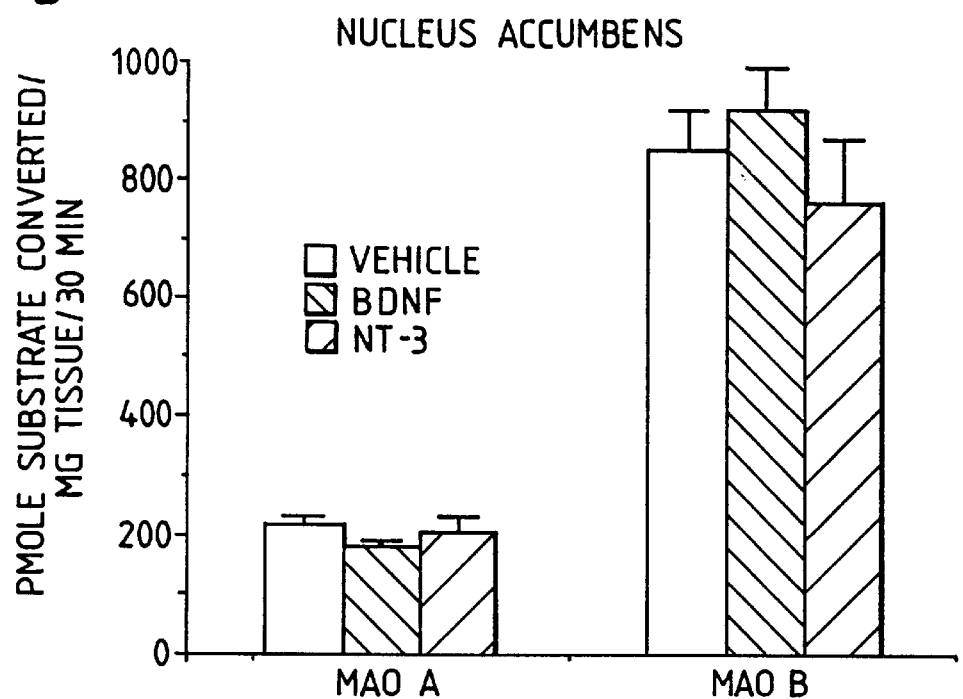
FIGS. 5A and 5B monoamine oxidase A and monoamine oxidase B (MAO A and MAO B) activities in the nucleus accumbens (FIG. 5A) and neostriatum (FIG. 5B) following 2 week bilateral nucleus accumbens infusions of BDNF or NT-3 were unchanged from vehicle-infused animals. Values are means±SEM, n=3–6/group.
Figure 5B:
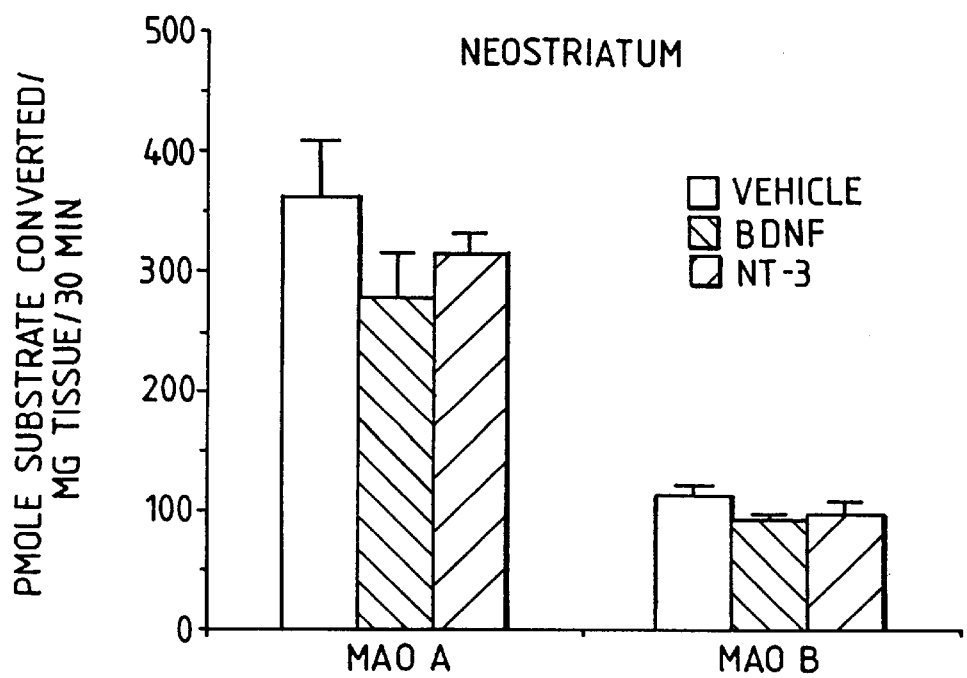

The MAO A and MAO B activities of the nucleus accumbens and neostriatum following 2 week bilateral nucleus accumbens infusions of BDNF or NT-3 were unchanged from vehicle-infused animals (FIGS. 5A and 5B) indicating that increased levels of serotonin metabolites following neurotrophin infusions were not due to increased MAO A activity, for which serotonin is a preferred substrate, or MAO B activity.

EXAMPLE 4

Hot-Plate Test

The hot-plate tests are conducted with an IITC model 39D Analgesia Meter. A rat is placed on a heated surface (54° C.). The surface is surrounded by a cylinder of clear plexiglass (10 in high). The latency between the time the rat is placed on the surface and the time it licks its hindpaw or attempts to escape is the hot plate latency. The animal is immediately removed from the apparatus at that time. One determination is recorded. To prevent tissue damage, the trial is terminated after 40 seconds if no response is observed.

Results

Figure 6:
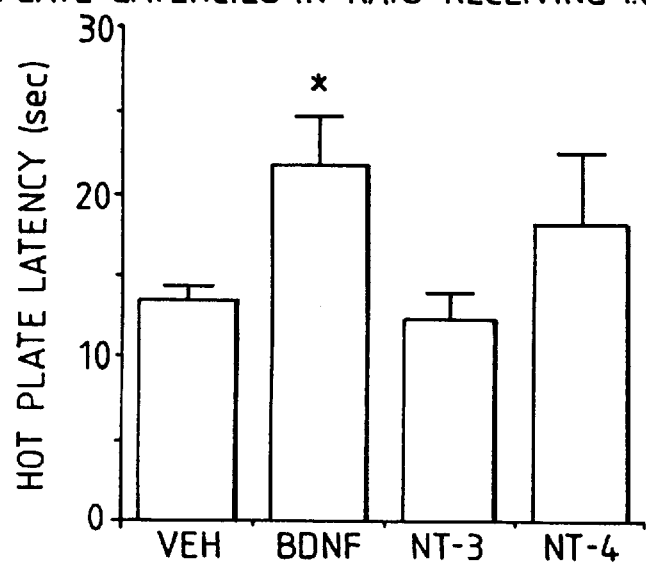
FIG. 6: Hot-plate latencies of rats receiving i.c.v. infusion of PBS vehicle (12 $\mu$l/day) or BDNF (24 $\mu$g/day), NT-3 (24 $\mu$g/day) or NT-4 (11.5 $\mu$g/day) for 1, 5 or 11 days. Values shown are mean±SEM for 7–8 rats per group.

The hot-plate latencies of rats infused for 7 days with phosphate buffered saline vehicle or neurotrophin are shown in FIG. 6. A one-way analysis of variance indicated a significant effect of treatment ($F_{3,28}=3.0$, $p<0.04$). A post-hoc Dunnett's t test revealed a significant analgesic effect of BDNF as compared to vehicle ($t=2.7$, $p<0.05$). Although an increase was observed in the hot-plate latency for NT-4 infused rats (18.2+4.3 vs. 13.5+0.9), this effect did not reach statistical significance. ($t=1.3$).

Discussion

In the hot plate test, only BDNF produced significant increases in the response latency. It seems likely that if the dose of NT-4 was increased to 24 μg/day (equal to the BDNF dose used), significant changes would also be seen for NT-4. Again, NT-3 is less potent than BDNF.

We claim:

1. A method of producing analgesia in a mammal comprising midbrain or intrathecal administration to the mammal of a pharmaceutically effective dose of at least one neurotrophin selected from the group consisting of brain derived neurotrophic factor, neurotrophin-3 and neurotrophin-4.

2. The method of claim 1, wherein the mammal is a human.

3. The method of claim 2 wherein said neurotrophin is human brain derived neurotrophic factor.

* * * * *